(12) United States Patent
Asherman

(10) Patent No.: US 6,613,006 B1
(45) Date of Patent: Sep. 2, 2003

(54) ORTHOPEDIC CAST AND METHOD OF MAKING THE SAME

(76) Inventor: Richard E. Asherman, P.O. Box 1298, Cody, WY (US) 82414

( * ) Notice: Subject to any disclaimer, the term of this patent is extended or adjusted under 35 U.S.C. 154(b) by 0 days.

(21) Appl. No.: 09/641,321

(22) Filed: Aug. 18, 2000

Related U.S. Application Data
(60) Provisional application No. 60/149,766, filed on Aug. 19, 1999.

(51) Int. Cl.$^7$ .................................................. A61F 5/00
(52) U.S. Cl. ................................ 602/5; 602/8; 602/20; 602/23
(58) Field of Search ........................... 602/1–8, 20, 23; 428/221, 224–227; 156/244.11, 224.12, 244.22, 244.24

(56) References Cited

U.S. PATENT DOCUMENTS

| | | | | |
|---|---|---|---|---|
| 4,273,115 A | | 6/1981 | Holland et al. ................ | 128/90 |
| 4,856,502 A | * | 8/1989 | Ersfeld et al. ................. | 602/8 |
| 5,584,800 A | * | 12/1996 | Scholz et al. .................. | 602/6 |
| 5,593,628 A | * | 1/1997 | Scholz et al. ................ | 264/154 |
| 5,716,661 A | * | 2/1998 | Scholz et al. .............. | 427/2.31 |
| 5,807,292 A | * | 9/1998 | Delmore ........................ | 602/8 |

\* cited by examiner

*Primary Examiner*—Nicholas D. Lucchesi
*Assistant Examiner*—Lalita M Hamilton
(74) *Attorney, Agent, or Firm*—Greenberg Traurig LLP; John R. Posthumus; Nancy L. Dempsey

(57) ABSTRACT

An immobilizing orthopedic cast includes a permanent immobilizing casting layer that incorporates a mesh design of rods aligned parallel and perpendicular to each other so as to create apertures in the surface of the immobilizing orthopedic cast. To stabilize the affected extremity, the immobilizing mesh cast is positioned around the affected extremity. The casting layer is made from a waterproof composite material that is pre-impregnated with a resin. The casting layer is cured via a reaction between the resin and a catalyst, thereby immobilizing the affected extremity to allow for healing. The apertures allow for ventilation of the affected extremity. The apertures further allow one to view the affected extremity. The apertures further allow one access to the affected extremity. The mesh design of the casting layer may be oriented in several different configurations. The casting layer may be supplied in various formats. A temporary inner protective sleeve layer may be used to increase the patient's comfort during the application of the permanent immobilizing casting layer to the affected extremity. The sleeve layer dissolves upon immersion of the affected extremity, the sleeve layer, and the casting layer in a liquid. Both water resistant padding material and medical dressing, may be used in conjunction with the immobilizing orthopedic cast. The method of making the immobilizing orthopedic cast includes applying a temporary inner protective sleeve layer to the affected extremity, applying the outer immobilizing casting layer to the affected extremity, and dissolving the temporary inner protective sleeve layer with a liquid.

48 Claims, 13 Drawing Sheets

ORTHOPEDIC CAST AND METHOD OF MAKING THE SAME

CROSS REFERENCE TO RELATED APPLICATIONS

This application claims priority under 35 U.S.C. Section 119 to prior U.S. Provisional application Ser. No. 60/149,766, filed Aug.19, 1999.

FIELD OF THE INVENTION

The present invention generally relates to casts for immobilizing a human extremity and a method of making the same.

BACKGROUND OF THE INVENTION

Traditional casting applications for fractures include plaster-of-paris casts and casts formed from glass fiber materials. Plaster-of-paris casts may be constructed by wrapping a fractured extremity and its surrounding area (the "affected body part" or "affected extremity") with wetted plaster-of-paris covered cloth strips to immobilize the body part upon the hardening of the plaster-of-paris. Casts formed from glass fiber materials may be wrapping an affected body part with a warm, flexible glass fiber fabric to immobilize the body part upon the cooling and stiffening of the glass fiber cast. Although these types of traditional casting applications are quite popular, each casting system has many associated drawbacks, including treatment-related problems and materials-related problems.

The treatment-related problems associated with traditional casting applications result from traditional casts prohibiting the affected body part covered by the cast from being adequately viewed and accessed the treatment of various maladies. For instance, edema, or the collection of fluid in bodily tissue, may occur in the soft tissue surrounding a fracture. With traditional casting applications, edema may go unnoticed until it causes circulatory impairment and/or excruciating pain, requiring cast removal and reapplication, or, in extreme circumstances, the loss of the extremity. Additionally, although current treatment protocol for edema calls for rest, immobilization, cold treatment, and elevation of the fractured limb, cold therapy cannot be applied directly to a casted extremity because the cast covers the affected body part.

Similarly, traditional casting applications also preclude the ability to visualize and topically treat any cutaneous wounds that may have been sustained before or in conjunction with the trauma that causes the fracture. Traditional casts also prevent the monitoring of the healing progress of these wounds, preventing health care providers from observing the wounds for signs of secondary infections. Secondary infections may be devastating in conjunction with fractures, requiring extensive antibiotic therapy, cast removal for observation and treatment, surgical debridement, and, in extreme cases, surgical amputations.

The probability for these types of complications is much greater in pediatric, geriatric, circulatory impaired and immune deficient patients. For example, pediatric patients may be unable to convey that their symptoms from complications are other than those common to fractures, resulting in delayed and prolonged treatment. In geriatric patients, decreased neurological function may result in symptoms going unnoticed by the patient until infection is beyond medicinal treatment, requiring cast removal, surgical intervention, and cast reapplication. For circulatory impaired and immune deficient patients, the decreased circulatory function or immune deficiency may result in prolonged healing periods and a reduction in the ability of the body to resist and fight infection, ultimately yielding the same results.

One materials-related problems associated with traditional casting applications is that traditional casts typically require cotton padding between the tissue of the affected body part and the cast. This padding inherently absorbs moisture, sweat, and water that may have been inadvertently introduced to the cast. Because of the lack of ventilation, the padding may retain this moisture for the duration of the casted period. The moisture and lack of ventilation provide an ideal environment for pathogenic microorganisms.

Also, both plaster and glass fiber casts are heavy and opaque, providing no ventilation to covered tissues. Severe itching may cause the patient to introduce a foreign object to scratch the itch, often resulting in abrasions to the covered tissue. Further, traditional plaster-of-paris casts degrade considerably when exposed to water.

Finally, of less significance to the healing process, but of considerable concern to patients, is the problems that the bulk of traditional casts pose on wardrobes. Most wardrobes will not accommodate the bulk and inflexibility of a cast on a limb, requiring either the purchase of new clothing to fit over the cast, or the splitting of the seams of current clothing to fit over the cast, thereby requiring the purchase of new clothing once the cast is removed.

BRIEF SUMMARY OF THE INVENTION

Thus, there is a need to provide a cast that is waterproof, ventilated, and capable of providing access to the affected area for observation and treatment. The present invention is a mesh cast comprising composite material and multiple apertures. It is desired to have mesh design having at least 40% apertures volume. The mesh cast is constructed of a composite waterproof material that is pre-impregnated with resin material, and is approximately 70% lighter and less bulky than current traditional casts. The mesh design allows for ventilation of cutaneous tissues by permitting air to flow freely over a fractured extremity and its immediately area (the "affected extremity"). The mesh design further allows one to view the cutaneous tissues to permit monitoring of the cutaneous tissue for signs of medical complications associated with fractures, including edema and secondary infection. The mesh cast further allows one to practice personal hygiene measures, such as bathing, directly through the cast. When applied to an affected extremity, the mesh cast secures the affected extremity to allow for healing of the fracture of the affected extremity such that the affected extremity is substantially immobilized.

The composite mesh cast allows the health care provider and the patient to immediately recognize and address edema, permitting early and rapid management. Additionally, cold therapy may be applied to the affected extremity without removal of the composite mesh cast. Similarly, the health care provider may perform a sensory nervous evaluation without removal of the composite mesh cast. Likewise, a Transcutaneous Electrical Nerve Stimulator ("TENS") unit may be used to relieve pain without removal of the composite mesh cast.

Because the patient may practice personal hygiene without removal of the composite mesh cast, and because of the increased ventilation associated with the composite mesh, severe itching is virtually eliminated. In the event that cutaneous wounds are sustained before or in conjunction with the trauma that caused the fracture, the mesh design allows for visualization and observation of wound healing and signs of secondary infections. Secondary infections may also be observed at the initial stages, and treated proactively with topical medications and oral antibiotics, eliminating the need for extensive antibiotic therapy, cast removal for observation and treatment, and surgical intervention. In the event that a primary infection is present prior to casting, wounds may be medicinally treated and their progress observed. Because it is unnecessary to use an absorbent such as cotton, with the composite mesh cast, the tissues are not in constant contact with moisture, and thus the ideal environment for pathogenic microorganisms is eliminated.

For high-risk patients such as pediatric, geriatric, circulatory impaired and immune deficient, these benefits associated with the composite mesh cast greatly reduce secondary complications which may have devastating impacts on these patients. For those patients with decreased neurological function (e.g., paraplegia, quadriplegia, etc.) signs of secondary infections may be noticed before the patient notices symptoms. For patients with decreased circulatory function or immune deficiency, complications may be observed and treated early, reducing or eliminating surgical intervention and prolonged healing regimens. Finally, because of the reduction in bulk of the composite mesh cast as compared to traditional plaster or fiberglass casts, patients may wear most clothing directly over the cast without alteration, thereby reducing the patient's cost for a new wardrobe.

BRIEF DESCRIPTION OF THE DRAWINGS

For a more complete understanding of the present invention, and further advantages thereof, reference is now made to the following detailed description taken in conjunction with the drawings in which.

DESCRIPTION OF THE INVENTION

Figure 1:
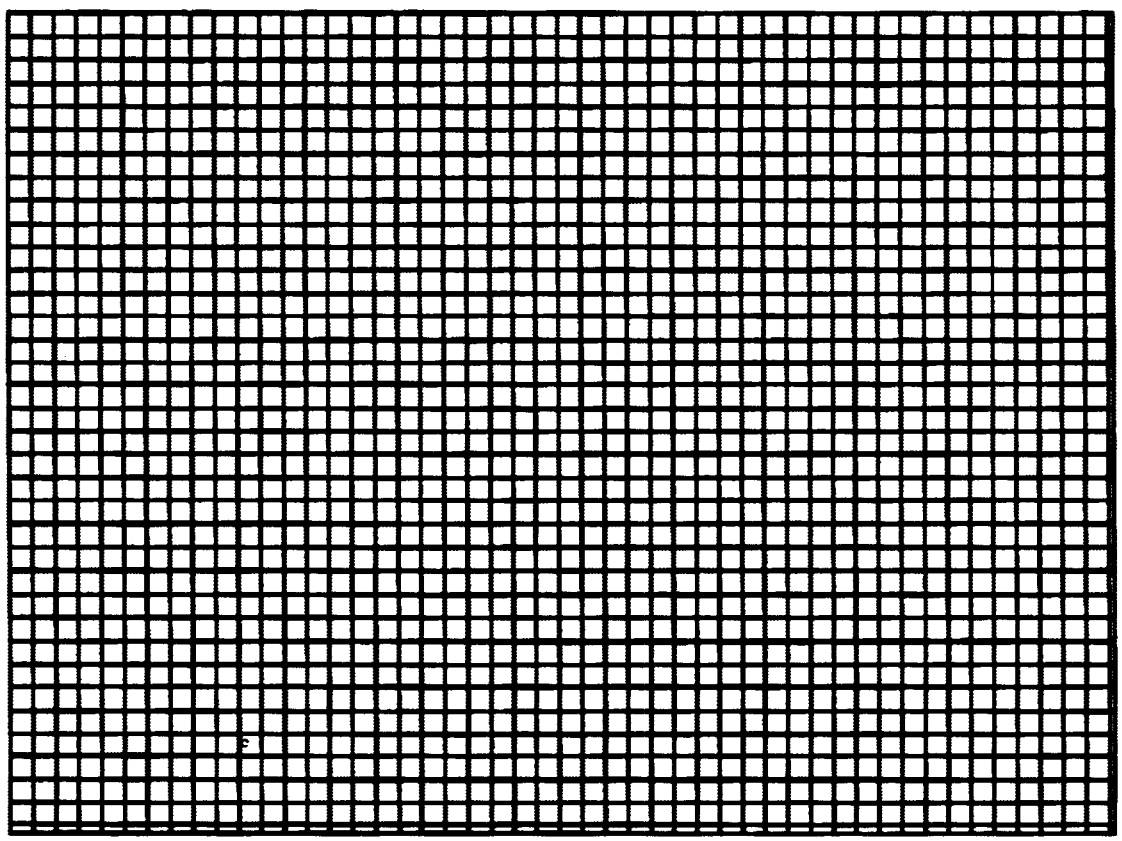
FIG. 1 is a perspective view of the material useable for immobilizing an affected extremity.
Figure 2A:
FIG. 2a is a horizontal cross-section of the material useable for immobilizing an affected extremity.
Figure 2B:
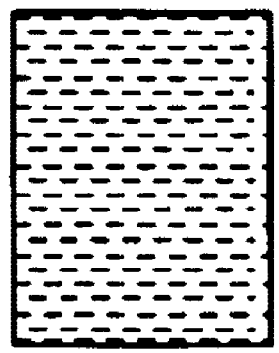
FIG. 2b is a vertical cross-section of the material containing a pre-impregnated resin useable for immobilizing an affected extremity.

Referring to FIG. 1, the present invention includes material 30 for immobilizing an affected extremity. The material 30 incorporates a mesh design 10 of rods 15 aligned parallel and perpendicular to each other so as to create apertures 20 in the surface of the mesh cast 5. The material 30 preferably comprises waterproof composite material such as, for example, carbon fiber or KEVLAR fiber. The material 30 is pre-impregnated with resin material 35. FIG. 2a shows a horizontal cross-section of the material 30. The borders 40 of the material 30 overlap so as to form a mesh cast 5 of substantially uniform thickness. FIG. 2b shows a vertical cross section of the material 30 containing pre-impregnated resin material 35.

Figure 3:
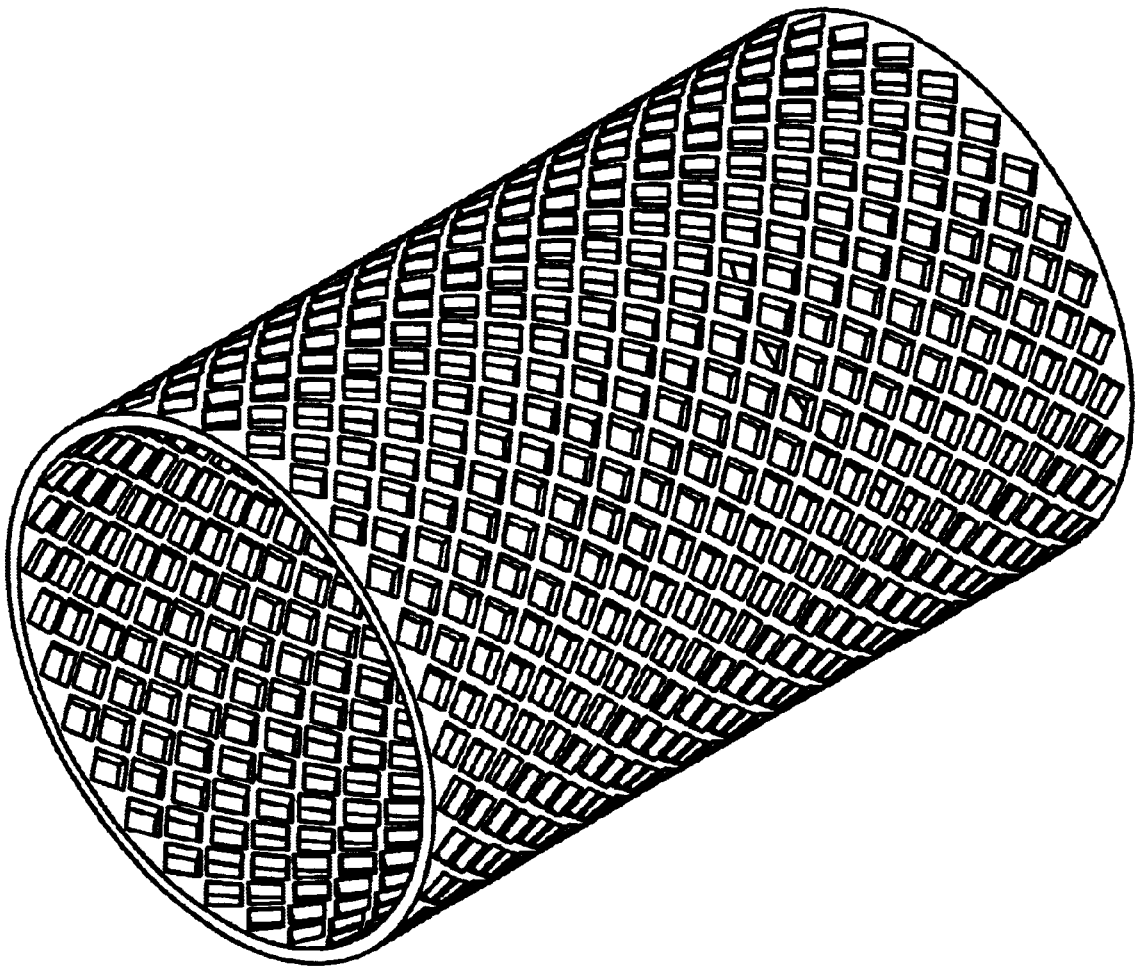
FIG. 3 is a side elevational view of the mesh cast having a mesh design oriented approximately 45 degrees offset from a border of the material.
Figure 4:
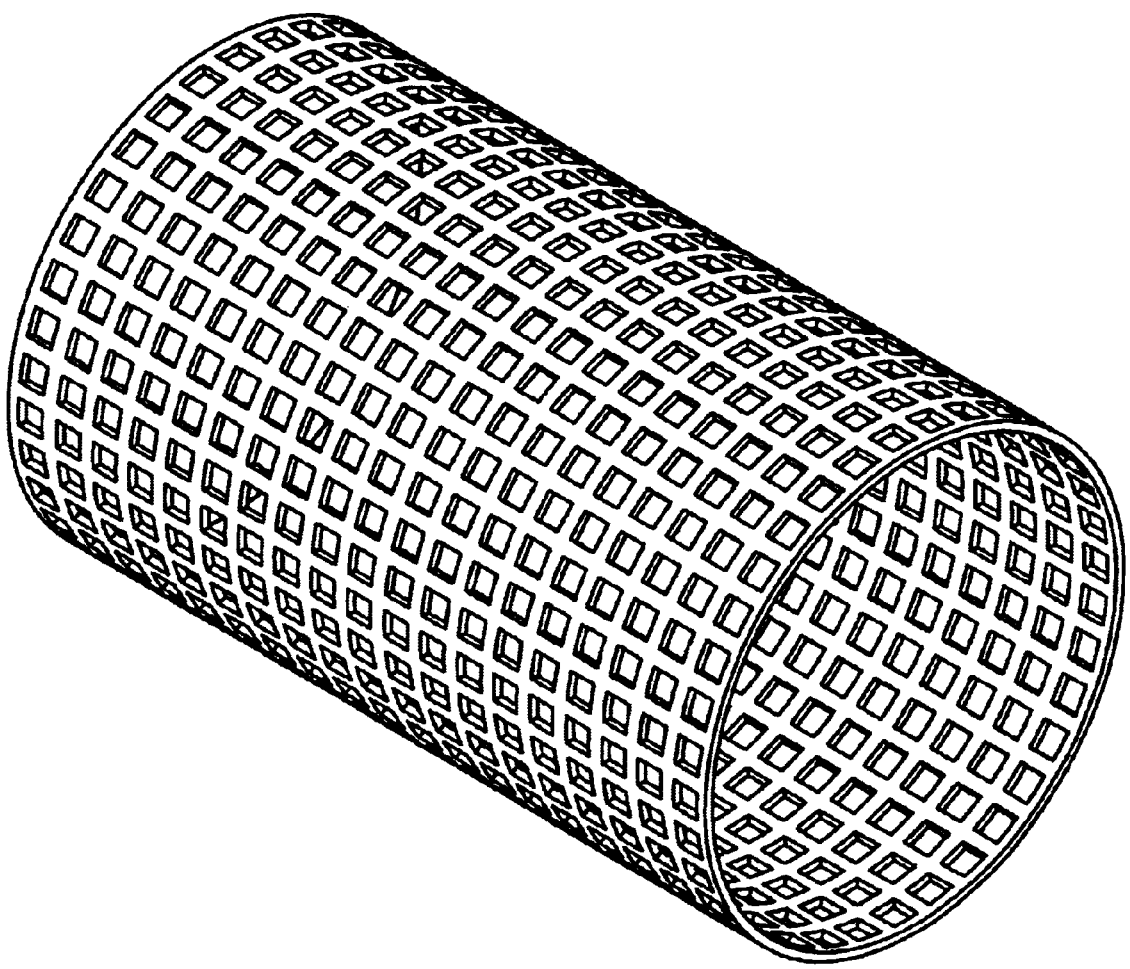
FIG. 4 is a side elevational view of the mesh cast having a mesh design oriented approximately 90 degrees offset from a border of the material

The mesh design 10 of the material 30 may be oriented in several different configurations. As shown in FIG. 3, in one embodiment of the invention, the mesh design 10 of the material 30 is oriented such that the rods 15 are offset at an angle of approximately 45 degrees from a border 40 of the material 30. As shown in FIG. 4, in another embodiment of the invention, the mesh design 10 of the material 30 is oriented such that the rods 15 are offset at an angle of approximately 90 degrees from a border 40 of the material 30.

Figure 5:
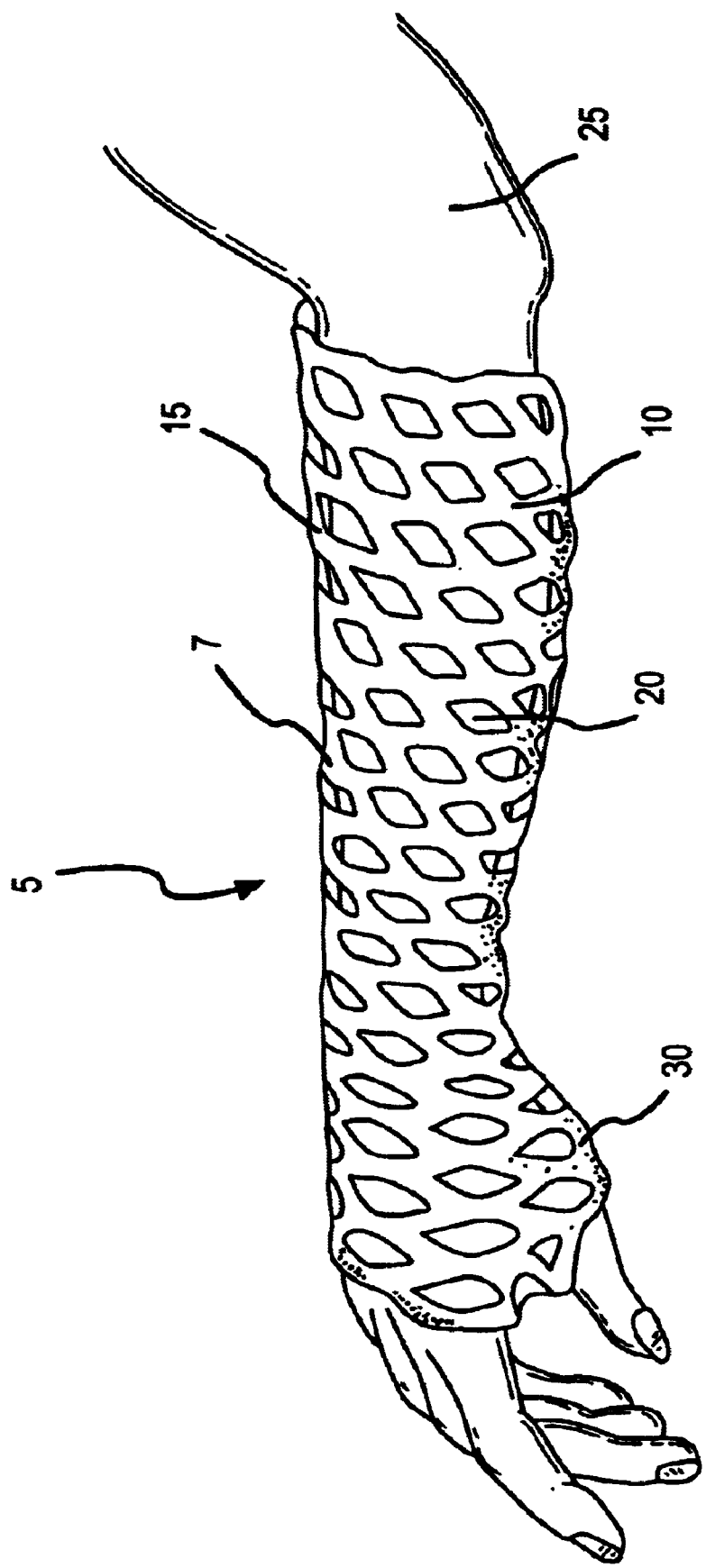
FIG. 5 is a side elevational view of the mesh cast useable to immobilize an affected extremity.

Referring to FIG. 5, one embodiment of the present invention includes a mesh cast 5, which is shown immobilizing a human wrist. The mesh cast 5 shown of FIG. 5 is formed by positioning the material 30 as a permanent immobilizing casting layer 7 around the affected extremity 25 and curing the material 30 until the mesh cast 5 is substantially rigid, thereby immobilizing the affected extremity 25.

The apertures 20 created by the alignment of the rods 15 of the mesh design 10 of the casting layer 7 create several advantages over traditional casts. For example, the apertures 20 permit substantial air-flow around the affected extremity 25, thereby ventilating the affected extremity 25. Additionally, the mesh cast 5 does not employ the typical cotton padding associated with traditional casts. The combination of these two factors allow for the mesh cast 5 to greatly reduce the presence of pathogenic microorganisms associated traditional casts.

Additionally, as compared to traditional opaque casts, the apertures 20 of the mesh cast 5 allow one to view the affected extremity 25. Thus, the mesh cast 5 allows for medical personnel to monitor any secondary infection or cutaneous legion present on the affected extremity 25.

Moreover, traditional casts do not allow for substantial access to the affected extremity 25. However, the apertures 20 of the mesh cast 5 permit medical personnel to access the affected extremity. For example, cold therapy may be applied to the affected extremity 25 without removal of the mesh cast 5.

Figure 6:
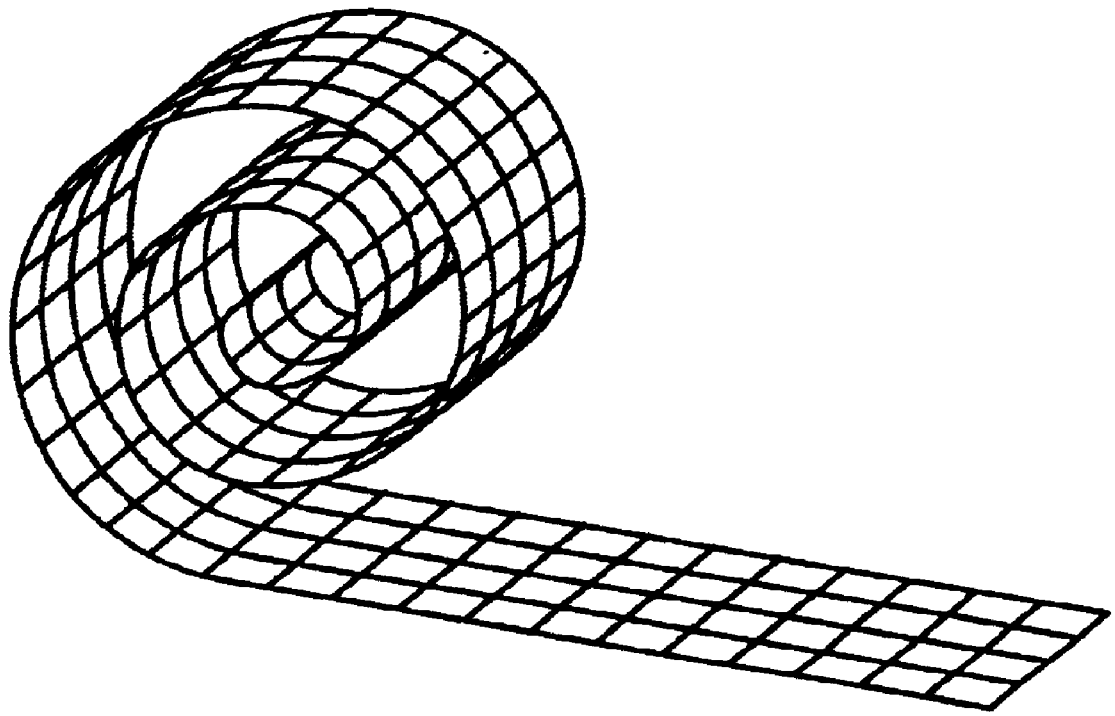
FIG. 6 is a side elevational view of the casting layer in roll format.

The material 30 of the present invention may be supplied in various formats. As shown in FIG. 6, in one embodiment of the invention the material 30 is in a roll format. In this embodiment, the material 30 is unrolled and wrapped around the affected extremity 25 to form a casting layer 7. The borders 40 of the material 30 casting layer 7 are tapered to overlap so as to form a mesh cast 5 of substantially uniform thickness. The casting layer 7 of the mesh cast 5 is cured via a reaction between the resin 35 and a catalyst such as, for example, air or electromagnetic energy such as, for example, ultraviolet light, such that the mesh cast 5 is substantially immobilized, thereby allowing the fractured affected extremity 25 to heal.

Figure 7:
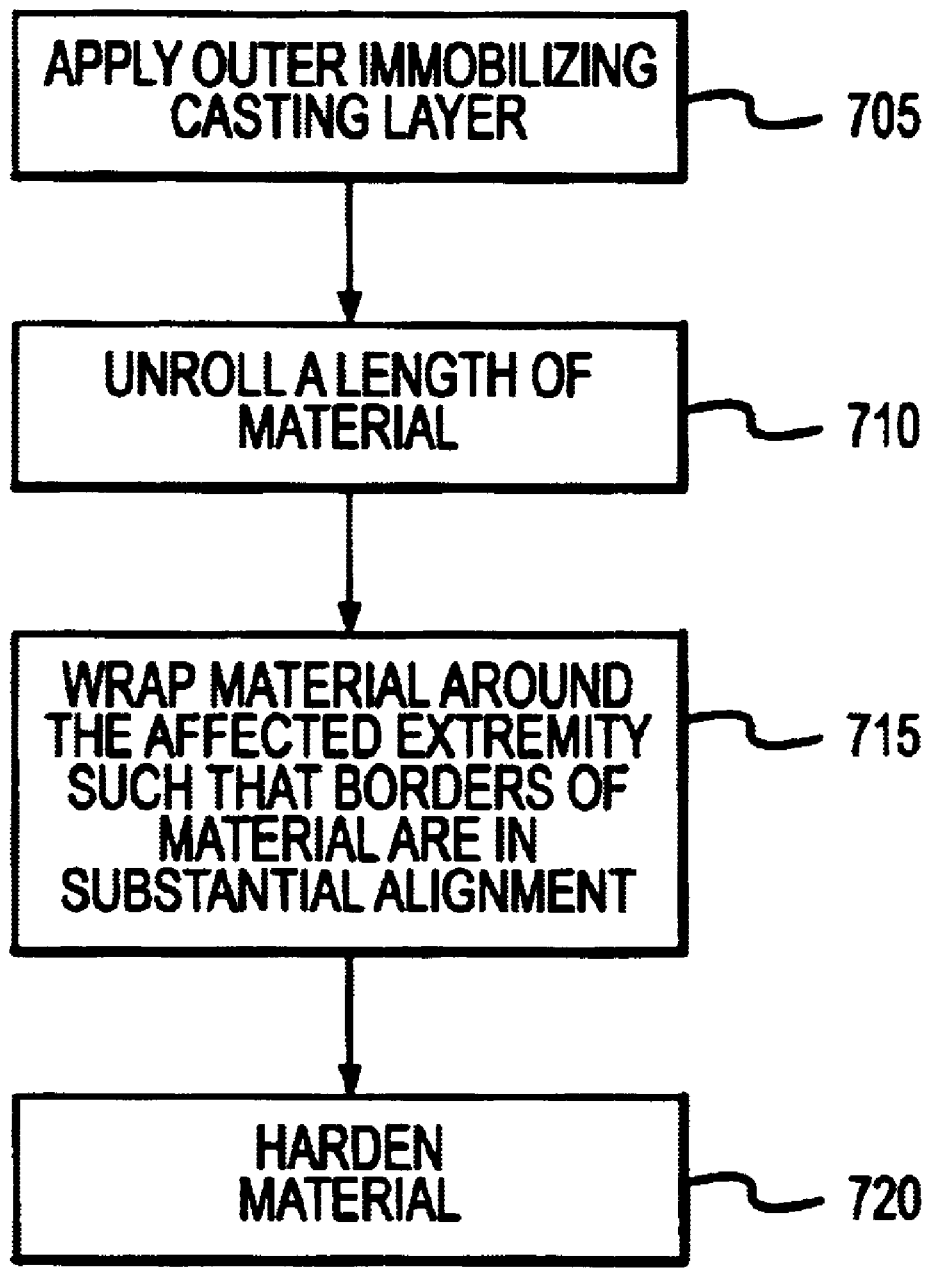
FIG. 7 is a flowchart for a method of making the mesh cast useable to immobilize an affected extremity with the casting layer in roll format.

FIG. 7 shows a flowchart of a method for making an mesh cast using material in a roll format. The illustrated process is initiated by applying 705 an outer immobilizing casting layer around the temporary inner protective sleeve by unrolling 710 a length of material and wrapping 715 the material around the affected extremity such that the borders of the material are in substantial alignment.

The process is then continued by hardening 720 the material via a reaction between the material and a catalyst such as, for example, air or electromagnetic energy such as, for example, ultraviolet light.

Figure 8:
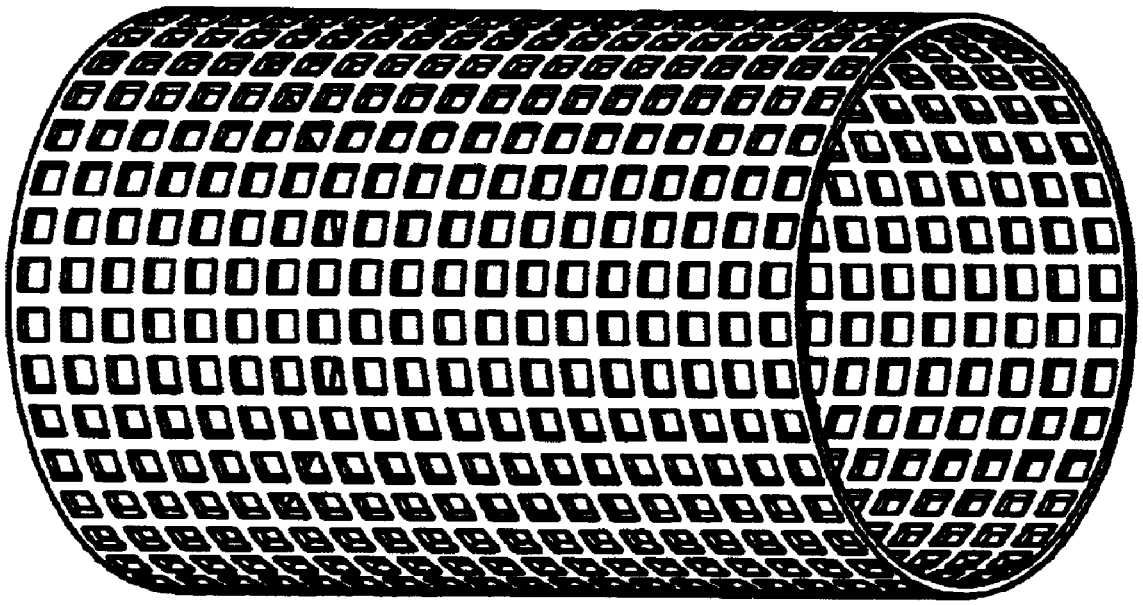
FIG. 8 is a side elevational view of the casting layer in sleeve format.

As shown in FIG. 8, in another embodiment of the invention the material 30 is in a sleeve format. In this embodiment, the material is fitted around the affected extremity 25 to form a casting layer 7.. The casting layer 7 of the mesh cast 5 is cured via a reaction between the resin 35 and a catalyst such as, for example, air or electromagnetic energy such as, for example, ultraviolet light, such that the mesh cast 5 is substantially immobilized, thereby allowing the fractured affected extremity 25 to heal.

Figure 9:
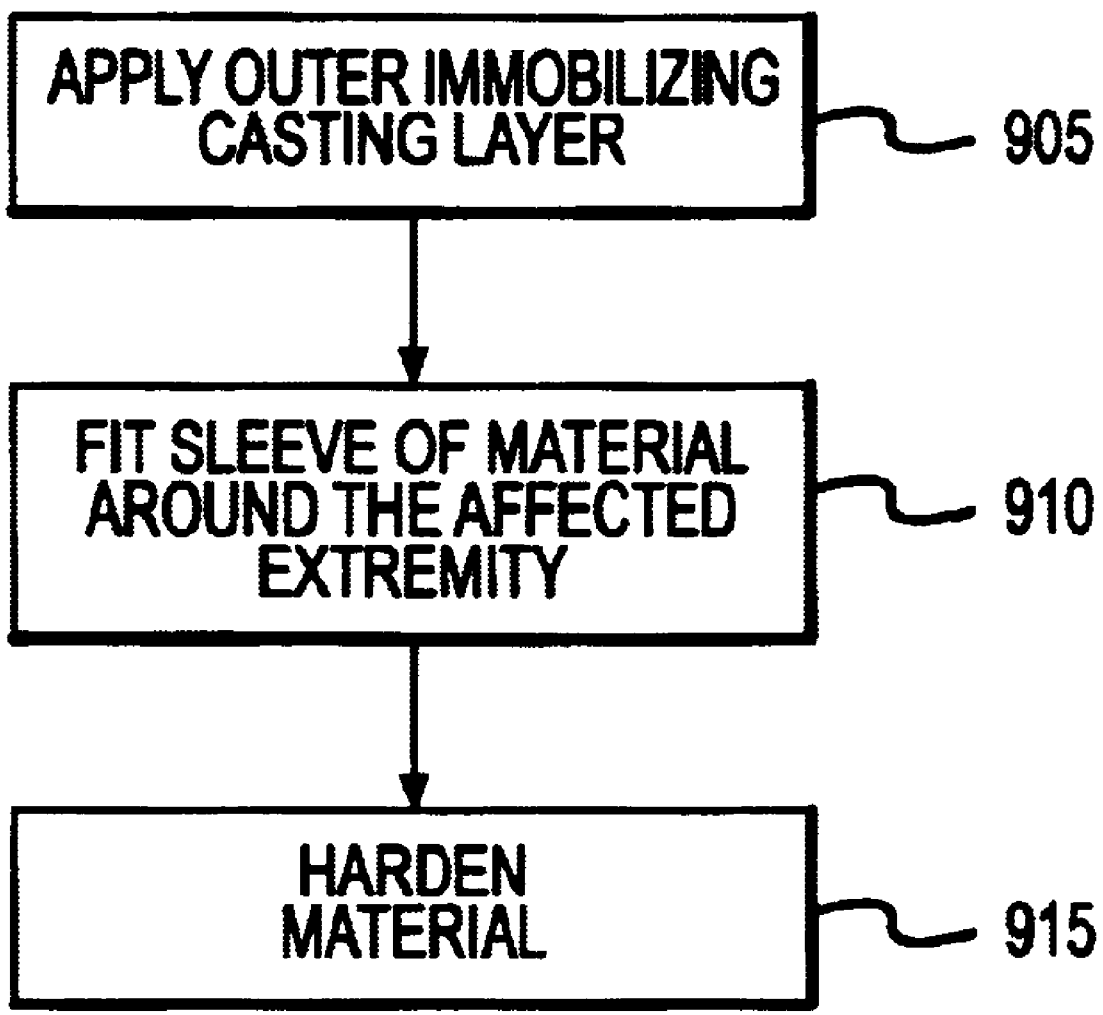
FIG. 9 is flowchart for a method of making the mesh cast useable to immobilize an affected extremity with the casting layer in sleeve format.

FIG. 9 shows a flowchart of a method for making an mesh cast using material in a sleeve format. The illustrated process is initiated by applying 905 an outer immobilizing casting layer around the temporary inner protective sleeve by fitting 910 the sleeve of material around the affected extremity.

The process is then continued by hardening 915 the material via a reaction between the material and a catalyst.

Figure 10:
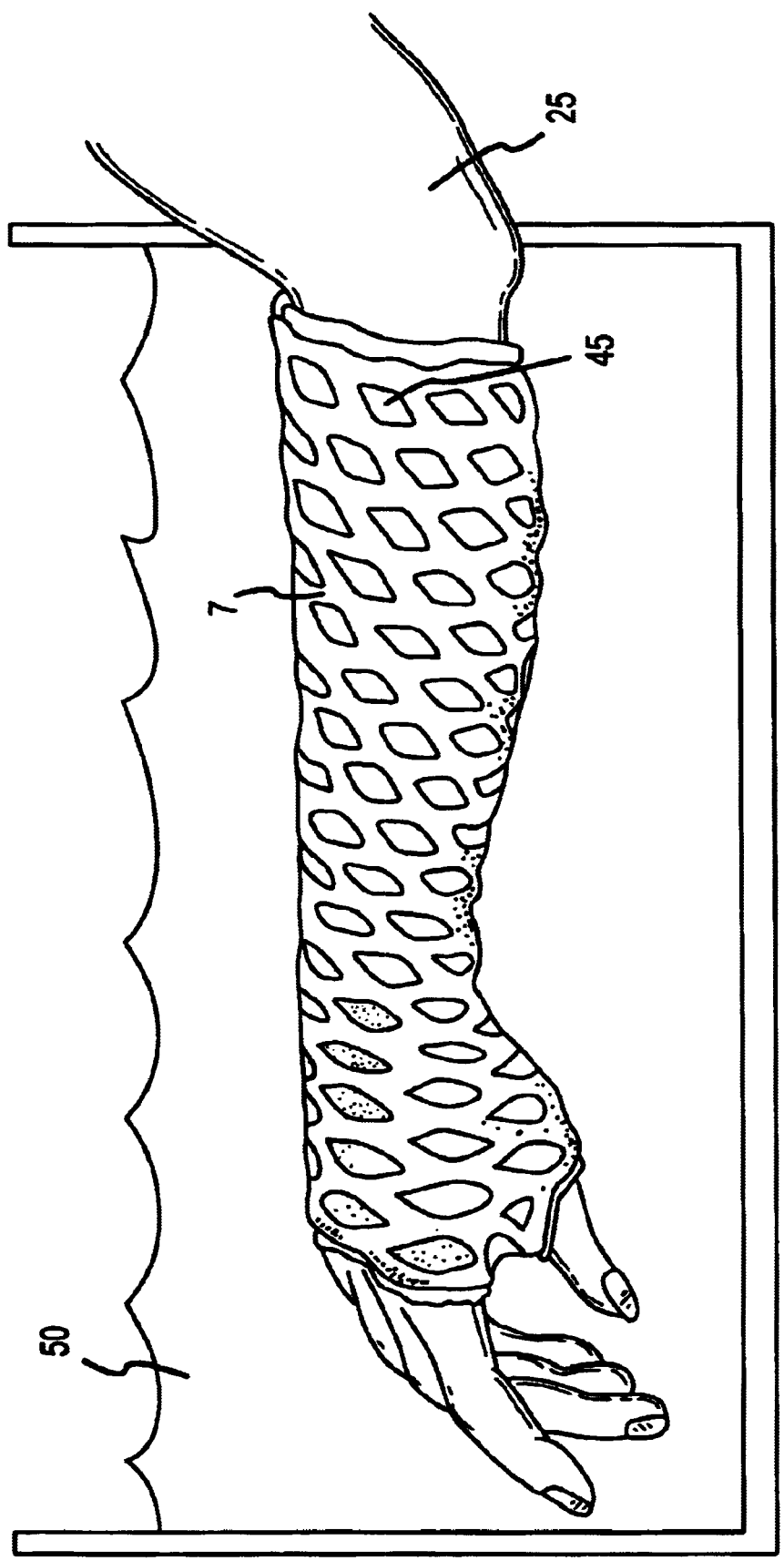
FIG. 10 is a side elevational view of the removal of the sleeve layer by immersing the affected extremity, sleeve layer and casting layer in a liquid.

Application of the material 30 as a casting layer 7 to the affected extremity 25 may cause slight discomfort to the patient, as the material 30 tends to be tacky upon application and create heat in setting. Thus, a temporary inner protective sleeve layer 45 may be used to increase the patient's comfort during the application of the casting layer 7 to the affected extremity 25. The sleeve layer 45 is made from a cellulose material capable of dissolving in a liquid 50. It will be appreciated that many different types of cellulose materials may be employed in this process. In one embodiment of the invention, the sleeve layer 45 is applied to the affected extremity 25 prior to the application of the casting layer 7. When the casting layer 7 is cured and is substantially rigid, the sleeve layer 45 may be dissolved by applying a liquid 50 to the sleeve layer 45. For example, as shown in FIG. 10, in one embodiment of the invention, the sleeve layer 45 dissolves upon immersion of the affected extremity 25, the sleeve layer 45, and the casting layer 7 in a liquid 50 such as, for example, water. It will be appreciated that many other liquids 50 could be used.

Figure 11:
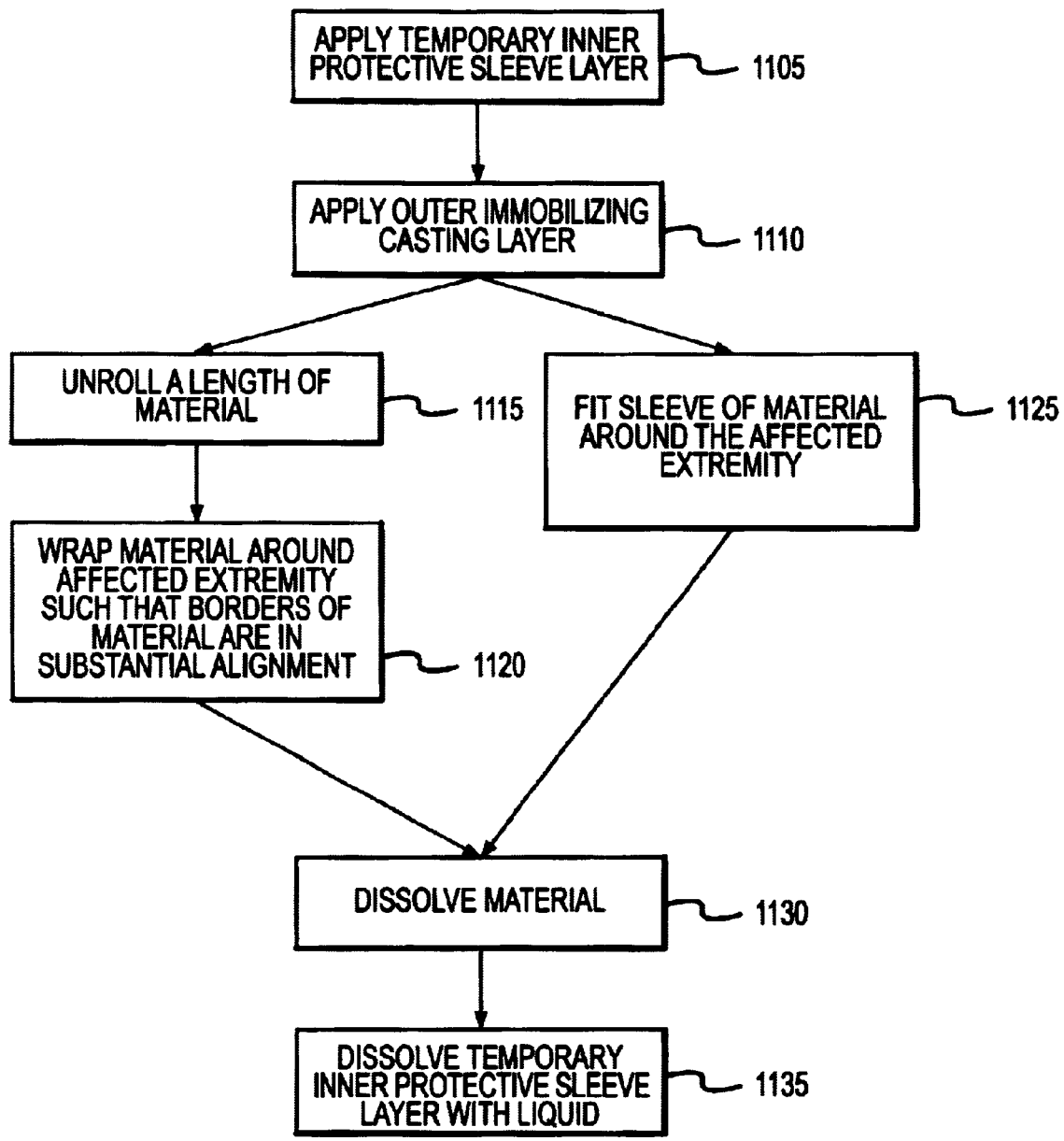
FIG. 11 is a flowchart of a method for making a mesh cast using material in conjunction with a temporary inner protective sleeve layer.

FIG. 11 shows a flowchart of a method for making an mesh cast using material in conjunction with a temporary inner protective sleeve layer. The illustrated process is initiated by applying 1105 a temporary inner protective sleeve layer adjacent an extremity to which the mesh cast is to be applied. This inner protective sleeve layer comprises a cellulose type material that is capable of dissolving in a liquid. It will be appreciated that many different types of cellulose materials may be employed in this process. Moreover, while water is one of the most readily available and mildest liquids for dissolving the temporary inner protective layer, it will be appreciated that many other liquids could be used.

The process is then continued by applying 1110 the outer immobilizing casting layer around the temporary inner protective sleeve. The outer immobilizing casting layer may be in either roll format or in sleeve format. If the outer immobilizing casting layer is in roll format, the process is continued by unrolling 1115 a length of material and wrapping 1120 the material around the affected extremity such that the borders of the material are in substantial alignment.

If the outer immobilizing casting layer is in sleeve format, the process is continued by fitting 1125 the sleeve of material around the affected extremity.

After the outer immobilizing casting layer is applied, the process is then continued by hardening 1130 the material via a reaction between the material and a catalyst.

The process is completed by dissolving 1135 the temporary inner protective layer with liquid, leaving the outer immobilizing casting layer fully intact.

Figure 12:
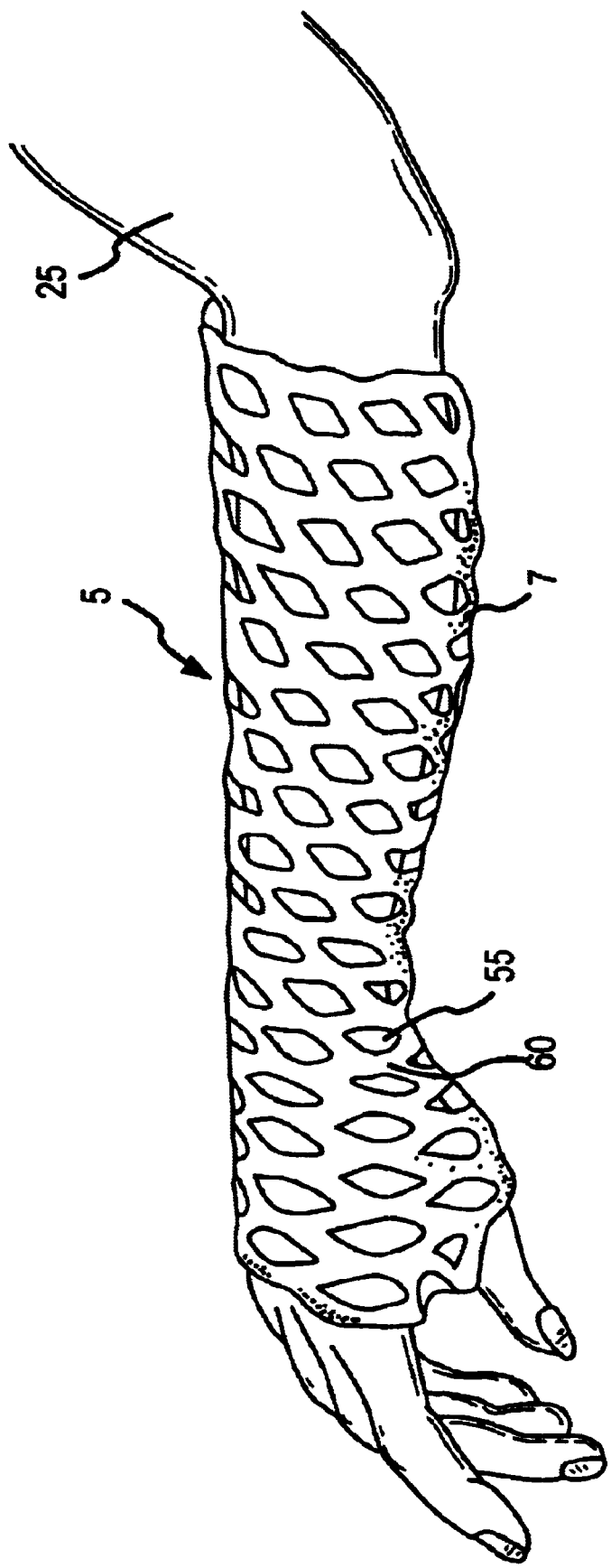
FIG. 12 is a side elevational view of padding material used in conjunction with the immobilizing orthopedic cast.

As shown in FIG. 12, to further enhance the comfort of the patient it will be appreciated that a water resistant padding material 55 may be applied to the affected extremity's 25 bony protrusions 60, such as, for example, a wrist or an ankle, to eliminate any discomfort associated with the rigid nature of the mesh cast 5. The padding material 55 is applied prior to the application of both the sleeve layer 45, if used, and the casting layer 7.

Figure 13:
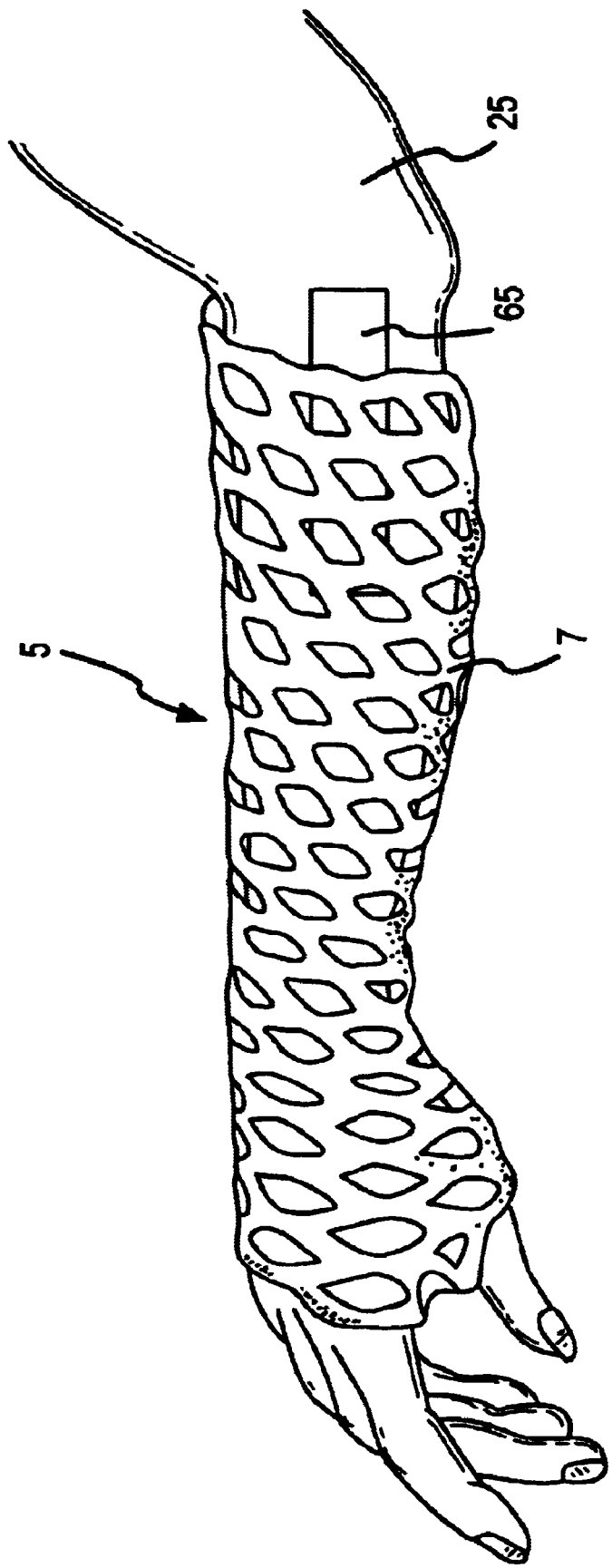
FIG. 13 is a side elevational view of medical dressing used in conjunction with the immobilizing orthopedic cast.

As shown in FIG. 13, it will further be appreciated that a medical dressing 65, such as, for example, gauze or a bandage, may be used in conjunction with the mesh cast 5. Similar to the padding material 55, the medical dressing 65 is applied to the affected extremity 25 prior to the application of both the sleeve layer 45, if used, and the casting layer 7.

The foregoing description of the present invention has been presented for purposes of illustration and description. The description is not intended to limit the invention to the form disclosed herein. Consequently, the invention and modifications commensurate with the above teachings and skill and knowledge of the relevant art are within the scope of the present invention. It is intended that the appended claims be construed to include all alternative embodiments as permitted by the prior art.

What is claimed is:

1. An immobilizing orthopedic cast, comprising:
 a permanent immobilizing casting layer,
 wherein said casting layer comprises a mesh design, said mesh design having at least 40 percent aperture volume,
 wherein said aperture volume permits at least partial visualization of an extremity to which said immobilizing orthopedic cast is to be applied,
 wherein said casting layer further comprises a composite material,
 wherein said composite material is pre-impregnated with a resin.

2. The immobilizing orthopedic cast as claimed in claim 1, wherein said composite material is waterproof.

3. The immobilizing orthopedic cast as claimed in claim 1, wherein said composite material comprises carbon fiber.

4. The immobilizing orthopedic cast as claimed in claim 1, wherein said composite material comprises fibers comprising poly-paraphenylene terephthalamide.

5. The immobilizing orthopedic cast as claimed in claim 1, wherein said mesh design is oriented at an angle of approximately 45 degrees offset from a border of said material.

6. The immobilizing orthopedic cast as claimed in claim 1, wherein said mesh design is oriented at an angle of approximately 90 degrees offset from a border of said material.

7. The immobilizing orthopedic cast as claimed in claim 1, in which said casting layer further comprises a material in a sleeve configuration.

8. The immobilizing orthopedic cast as claimed in claim 1, in which said casting layer further comprises a material in a roll configuration.

9. The immobilizing orthopedic cast as claimed in claim 1, further comprising a temporary inner protective sleeve layer adjacent an extremity to which said immobilizing orthopedic cast is to be applied.

10. The immobilizing orthopedic cast as claimed in claim 9, wherein said temporary inner protective sleeve layer comprises a cellulose material capable of dissolving in a liquid.

11. The immobilizing orthopedic cast as claimed in claim 1, wherein said aperture volume permits substantial ventilation of an extremity to which said immobilizing orthopedic cast is to be applied.

12. The immobilizing orthopedic cast as claimed in claim 1, further comprising a layer of padding fixedly positioned between said casting layer and a bony protrusion of an extremity to which said immobilizing orthopedic cast is to be applied.

13. The immobilizing orthopedic cast as claimed in claim 1, further comprising a layer of padding fixedly positioned between said casting layer and a cutaneous lesion of an extremity to which said immobilizing orthopedic cast is to be applied.

14. A method for making an immobilizing orthopedic cast, comprising the steps of:
    applying a temporary inner protective sleeve layer adjacent an extremity to which said immobilizing orthopedic cast is to be applied, said temporary inner protective sleeve comprising a cellulose material capable of dissolving in a liquid;
    applying an outer immobilizing casting layer positioned around said temporary inner protective sleeve, said outer immobilizing casting layer comprising a composite material, wherein said outer immobilizing casting layer further comprises a mesh design having at least 40 percent aperture volume, wherein said aperture volume permits at least partial visualization of an extremity to which said immobilizing orthopedic cast is to be applied; and
    dissolving said temporary inner protective sleeve with said liquid.

15. The method as claimed in claim 14, wherein said outer immobilizing casting layer is waterproof.

16. The method as claimed in claim 14, wherein said composite material comprises carbon fiber.

17. The method as claimed in claim 14, wherein said composite material comprises fibers comprising poly-paraphenylene terephthalamide.

18. The method as claimed in claim 14, wherein said mesh design is oriented at an angle of approximately 45 degrees offset from a border of said material.

19. The method as claimed in claim 14, wherein said mesh design is oriented at an angle of approximately 90 degrees offset from a border of said material.

20. The method as claimed in claim 14, wherein said outer immobilizing casting layer further comprises a material in a sleeve configuration.

21. The method as claimed in claim 14, wherein said outer immobilizing casting layer further comprises a material in a roll configuration.

22. The method as claimed in claim 14, wherein said aperture volume permits substantial ventilation of an extremity to which said immobilizing orthopedic cast is to be applied.

23. The method as claimed in claim 14, further comprising the step of:
    applying a layer of padding between said outer immobilizing casting layer and a bony protrusion on an extremity to which said immobilizing orthopedic cast is to be applied.

24. The method as claimed in claim 14, further comprising the step of:
    applying a layer of padding between said outer immobilizing casting layer and a cutaneous lesion of in extremity to which said immobilizing orthopedic cast is to be applied.

25. An immobilizing orthopedic cast, comprising:
    a permanent immobilizing casting layer,
    wherein said casting layer comprises a mesh design, said mesh design having at least 40 percent aperture volume,
    wherein said aperture volume permits at least partial access to an extremity to which said immobilizing orthopedic cast is to be applied,
    wherein said casting layer further comprises a composite material,
    wherein said composite material is pre-impregnated with a resin.

26. The immobilizing orthopedic cast as claimed in claim 25, wherein said composite material is waterproof.

27. The immobilizing orthopedic cast as claimed in claim 25, wherein said composite material comprises carbon fiber.

28. The immobilizing orthopedic cast as claimed in claim 25, wherein said composite material comprises fibers comprising poly-paraphenylene terephthalamide.

29. The immobilizing orthopedic cast as claimed in claim 25, wherein said mesh design is oriented at an angle of approximately 45 degrees offset from a border of said material.

30. The immobilizing orthopedic cast as claimed in claim 25, wherein said mesh design is oriented at an angle of approximately 90 degrees offset from a border of said material.

31. The immobilizing orthopedic cast as claimed in claim 25, in which said casting layer further comprises a material in a sleeve configuration.

32. The immobilizing orthopedic cast as claimed in claim 25, in which said casting layer further comprises a material in a roll configuration.

33. The immobilizing orthopedic cast as claimed in claim 25, further comprising a temporary inner protective sleeve layer adjacent an extremity to which said immobilizing orthopedic cast is to be applied.

34. The immobilizing orthopedic cast as claimed in claim 33, wherein said temporary inner protective sleeve layer comprises a cellulose material capable of dissolving in a liquid.

35. The immobilizing orthopedic cast as claimed in claim 25, wherein said aperture volume permits substantial ventilation of an extremity to which said immobilizing orthopedic cast is to be applied.

36. The immobilizing orthopedic cast as claimed in claim 25, further comprising a layer of padding fixedly positioned between said casting layer and a bony protrusion of an extremity to which said immobilizing orthopedic cast is to be applied.

37. The immobilizing orthopedic cast as claimed in claim 25, further comprising a layer of padding fixedly positioned between said casting layer and a cutaneous lesion of an extremity to which said immobilizing orthopedic cast is to be applied.

38. A method for making an immobilizing orthopedic cast, comprising the steps of:

applying a temporary inner protective sleeve layer adjacent an extremity to which said immobilizing orthopedic cast is to be applied, said temporary inner protective sleeve comprising a cellulose material capable of dissolving in a liquid;

applying an outer immobilizing casting layer positioned around said temporary inner protective sleeve, said outer immobilizing casting layer comprising a composite material, wherein said outer immobilizing casting layer further comprises a mesh design having at least 40 percent aperture volume, wherein said aperture volume permits at least partial access to an extremity to which said immobilizing orthopedic cast is to be applied; and dissolving said temporary inner protective sleeve with said liquid.

39. The method as claimed in claim 38, wherein said outer immobilizing casting layer is waterproof.

40. The method as claimed in claim 38, wherein said composite material comprises carbon fiber.

41. The method as claimed in claim 38, wherein said composite material comprises fibers comprising polyparaphenylene terephthalamide.

42. The method as claimed in claim 38, wherein said mesh design is oriented at an angle of approximately 45 degrees offset from a border of said material.

43. The method as claimed in claim 38, wherein said mesh design is oriented at an angle of approximately 90 degrees offset from a border of said material.

44. The method as claimed in claim 38, wherein said outer immobilizing casting layer further comprises a material in a sleeve configuration.

45. The method as claimed in claim 38, wherein said outer immobilizing casting layer further comprises a material in a roll configuration.

46. The method as claimed in claim 38, wherein said aperture volume permits substantial ventilation of an extremity to which said immobilizing orthopedic cast is to be applied.

47. The method as claimed in claim 38, further comprising the step of:

applying a layer of padding between said outer immobilizing casting layer and a bony protrusion on an extremity to which said immobilizing orthopedic cast is to be applied.

48. The method as claimed in claim 38, further comprising the step of applying a layer of padding between said outer immobilizing casting layer and a cutaneous lesion of an extremity to which said immobilizing orthopedic cast is to be applied.

* * * * *